United States Patent [19]

Barlow et al.

[11] 4,399,138
[45] Aug. 16, 1983

[54] ALKANOLAMINE DERIVATIVES

[75] Inventors: Jeffrey J. Barlow, Stockport; Leslie H. Smith, Cheadle, both of England

[73] Assignee: Imperial Chemical Industries PLC, London, England

[21] Appl. No.: 344,969

[22] Filed: Feb. 2, 1982

[30] Foreign Application Priority Data

Feb. 2, 1981 [GB] United Kingdom ............. 8103131

[51] Int. Cl.³ ............... C07D 241/16; C07D 241/26; A61K 31/495
[52] U.S. Cl. ............................ 424/250; 424/248.4; 544/134; 544/407; 544/409
[58] Field of Search ............. 544/407, 408, 409, 410, 544/134; 424/250, 248.4

[56] References Cited

U.S. PATENT DOCUMENTS

| | | | |
|---|---|---|---|
| 3,544,568 | 12/1970 | Cragoe et al. | 544/407 |
| 3,577,418 | 5/1971 | Cragoe et al. | 544/407 |
| 3,655,663 | 4/1972 | Wasson et al. | 544/134 |
| 4,034,106 | 7/1977 | Smith | 424/304 |
| 4,115,409 | 9/1978 | Large et al. | 544/35 |
| 4,115,575 | 9/1978 | Frei et al. | 544/408 |
| 4,139,623 | 2/1979 | Jaeggi et al. | 544/408 |
| 4,211,878 | 7/1980 | Smith | 424/275 |
| 4,219,561 | 8/1980 | Smith et al. | 424/304 |
| 4,221,807 | 9/1980 | Smith | 424/278 |

Primary Examiner—Donald G. Daus
Assistant Examiner—H. Hendricks
Attorney, Agent, or Firm—Cushman, Darby & Cushman

[57] ABSTRACT

Novel alkanolamine derivatives of the formula:

$Ar-OCH_2.CHOH.CH_2-NH-A^1-NHCO-$

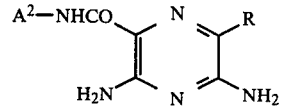

wherein
Ar is phenyl or naphthyl which is unsubstituted or which bears one or two substituents selected from halogen, trifluoromethyl, hydroxy, amino, nitro, carbamoyl, carbamoylmethyl and cyano, and alkyl, alkenyl, alkoxy, alkenyloxy, alkylthio, alkanoyl and alkanoylamino each of up to 6 carbon atoms, or Ar is 4-indolyl, 4-benzo[b]thienyl, 5-benzo[1,4]dioxanyl, 4- or 5-indanyl, 5- or 6- 1,2,3,4-tetrahydronaphthyl), 2,3-dihydroxy-1,2,3,4-tetrahydronaphth-5-yl or 4- morpholino-1,2,5-thiadiazol-3-yl;
wherein R is halogen;
wherein $A^1$ is alkylene of 2 to 6 carbon atoms; and
wherein $A^2$ is alkylene of 1 to 7 carbon atoms which in unsubstituted or bears a phenyl, hydroxy or carbamoyl substituent, or $A^2$ is cycloalkylene of 3 to 6 carbon atoms;
or acid-addition salts thereof.

The compounds possess either β-adrenergic blocking activity or diuretic activity or both such activities and may be used in the treatment of heart disease or hypertension. Also disclosed are processes for the manufacture of the compounds and pharmaceutical compositions containing them.

7 Claims, No Drawings

ALKANOLAMINE DERIVATIVES

This invention relates to new alkanolamine derivatives some of which possess a high level of β-adrenergic blocking activity, some of which possess diuretic activity and some of which possess both β-adrenergic blocking activity and diuretic activity.

Many β-adrenergic blocking agents are known, most of which are 1-amino-3-aryloxypropan-2-ol derivatives, and some of these, which are described for example in United Kingdom Patent Specifications Nos. 1,455,116; 1,457,876; 1,509,527 and 1,540,463, have the general formula:

Ar—OCH$_2$.CHOH.CH$_2$—NH—A—NHCO—R$^{10}$ wherein Ar is an aromatic or heterocyclic substituent, A is alkylene and R$^{10}$ is a hydrocarbyl or heterocyclyl substituent, or such a substituent linked by a linking group.

Many diuretic agents are known, and amongst these is a commercially-available compound known as AMILORIDE which has the formula:

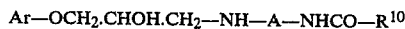
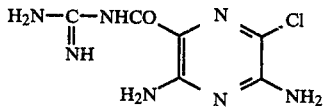

It is also known to prepare a pharmaceutical composition containing both a diuretic and a β-adrenergic blocking agent. For example, compositions containing atenolol and chlorthalidone, or propranolol and bendrofluazide, are commercially available. However, no single chemical compound which possessed both activities to a significant extent was hitherto available, and in particular no such compound is known which possesses both activities at a clinically-effective dose.

According to the present invention there is provided an alkanolamine derivative of the formula:

Ar—OCH$_2$.CHOH.CH$_2$—NH—A$^1$—NHCO—

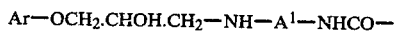
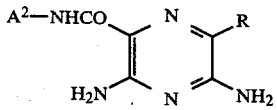

wherein

Ar is phenyl or naphthyl which is unsubstituted or which bears one or two substituents selected from halogen, trifluoromethyl, hydroxy, amino, nitro, carbamoyl, carbamoylmethyl and cyano, and alkyl, alkenyl, alkoxy, alkenyloxy, alkylthio, alkanoyl and alkanoylamino each of up to 6 carbon atoms, or Ar is 4-indolyl, 4-benzo[b]thienyl, 5-benzo[1,4]dioxanyl, 4- or 5-indanyl, 5- or 6-(1,2,3,4-tetrahydronaphthyl), 2,3-dihydroxy-1,2,3,4-tetrahydronaphth-5-yl or 4-morpholino-1,2,5-thiadiazol-3-yl;

wherein R is halogen;

wherein A$^1$ is alkylene of 2 to 6 carbon atoms; and wherein A$^2$ is alkylene of 1 to 7 carbon atoms which is unsubstituted or bears a phenyl, hydroxy or carbamoyl substituent, or A$^2$ is cycloalkylene of 3 to 6 carbon atoms;

or an acid-addition salt thereof.

It will be observed that the alkanolamine derivative of the invention possesses at least one asymmetric carbon atom, namely the carbon atom of the —CHOH— group in the alkanolamine side-chain, and when A$^1$ or A$^2$ is branched-chain alkylene it may possess further asymmetrical carbon atoms, and it can therefore exist in racemic and optically-active forms. It is to be understood that this invention encompasses the racemic form of the alkanolamine derivative and any optically-active form which possesses either β-adrenergic blocking activity or diuretic activity, or both such activities, it being a matter of common general knowledge how a racemic compound may be resolved into optically-active forms, and how the β-adrenergic blocking and-/or diuretic activity of these forms may be determined. It is further to be understood that β-adrenergic blocking activity usually predominates in that optically-active form which has the "S" absolute configuration of the said —CHOH— group.

A suitable value for the one or two substituents in Ar when it is phenyl or naphthyl is, for example, one or two substituents selected from fluoro, chloro, bromo, iodo, trifluoromethyl, hydroxy, amino, nitro, carbamoyl, carbamoylmethyl, cyano, methyl, ethyl, n-propyl, t-butyl, allyl, methoxy, isopropoxy, allyloxy, methylthio, formyl, acetyl and acetamido substituents.

A suitable value for R is fluorine, chlorine, bromine or iodine. R is preferably chlorine.

A suitable value for A$^1$ is, for example, ethylene, 1-methylethylene, 1,1-dimethylethylene or hexamethylene. A$^1$ is preferably ethylene or 1,1-dimethylethylene.

A suitable value for A$^2$ is, for example, methylene or ethylene, or it has the formula —CR$^1$R$^2$— wherein R$^1$ is hydrogen or alkyl of up to 3 carbon atoms and R$^2$ is alkyl of up to 3 carbon atoms which is unsubstituted or which bears a phenyl, hydroxy or carbamoyl substituent, or R$^1$ and R$^2$ are joined to form alkylene of 2 to 5 carbon atoms. Preferably R$^1$ is hydrogen or methyl and R$^2$ is methyl, ethyl, isopropyl, benzyl or hydroxymethyl, or R$^1$ and R$^2$ are joined to form ethylene (that is to form a cyclopropyl group).

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, succinate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

A preferred alkanolamine derivative of the invention which possesses a high level of β-adrenergic blocking activity is a compound of the formula given above wherein Ar is unsubstituted naphthyl, preferably α-naphthyl, or Ar is phenyl which is unsubstituted or which bears one halogen, carbamoyl, carbamoylmethyl, cyano, alkyl, alkoxy, alkenyl, alkenyloxy, alkanoyl or alkanoylamino substituent, or Ar is 4-indolyl, 4-benzo[b]thienyl, 5benzo[1,4]dioxanyl, 4-indanyl, 5-(1,2,3,4-tetrahydronaphthyl), 2,3-dihydroxy-1,2,3,4-tetrahydronaphth-5-yl or 4-morpholino-1,2,5-thiadiazol-3-yl; wherein R is chlorine, wherein A$^1$ is ethylene or 1,1-dimethylethylene[—C(CH$_3$)$_2$CH$_2$—], wherein A$^2$ is methylene, ethylene, ethylidene[—CH(CH$_3$)—] or 1-methylethylidene [—C(CH$_3$)$_2$—, that is —CR$^1$R$^2$— wherein R$^1$ and R$^2$ are both methyl], or is an acid-addition salt thereof.

A preferred alkanolamine derivative of the invention which possesses diuretic activity is a compound of the formula given above wherein Ar and $A^1$ have any of the meanings stated above, wherein R is chlorine and wherein $A^2$ is $-CR^1R^2-$ wherein $R^1$ and $R^2$ have any of the meanings stated above.

As a general trend, an alkanolamine derivative of the invention will have diuretic activity if $A^2$ is $-CR^1R^2-$, that is, if only one carbon atom separates the adjacent $-CO-$ and $-NH-$ groups. If the number of carbon atoms in the group $-CR^1R^2-$ exceeds 3, the alkanolamine derivative will have relatively poor $\beta$-adrenergic blocking activity, and if $-CR^1R^2-$ is $-C(CH_3)_2-$, that is, having exactly 3 carbon atoms, the alkanolamine derivative will also have relatively poor $\beta$-adrenergic blocking activity when Ar is $\beta$-naphthyl or $\beta$-tetrahydronaphthyl, or is $\alpha$-naphthyl bearing 2 additional substituents. Such compounds having poor $\beta$-adrenergic blocking activity all, however possess diuretic activity. In order to obtain an alkanolamine derivative which possesses both $\beta$-adrenergic blocking activity and diuretic activity, the value for Ar should be selected from those set out in the penultimate paragraph above, and $A^2$ should be $-CR^1R^2-$ as defined above.

Specific alkanolamine derivatives of the invention are those hereinafter described in the Examples. Of these a preferred compound, by virtue of its high level both of $\beta$-adrenergic blocking activity and diuretic activity, is 3,5-diamino-6-chloro-N-{1-[N-$\beta$-(2-hydroxy-3-$\alpha$-naphthoxypropylamino)-ethylcarbamoyl]-1-methylethyl}-pyrazine-2-carboxamide or an acid-addition salt thereof.

The alkanolamine derivatives of the invention may be manufactured by any chemical process known to be useful for the manufacture of chemically-analogous compounds.

A preferred process for the manufacture of an alkanolamine derivative of the invention comprises the reaction of a compound of the formula:

Ar—OCH$_2$.CHOH.CH$_2$—NH—A$^1$—NH$_2$ wherein Ar and $A^1$ have the meanings stated above, with an acid of the formula:

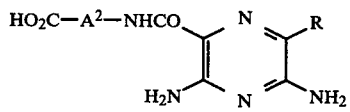

wherein R and $A^2$ have the meanings stated above, or a reactive derivative thereof.

A suitable reactive derivative is, for example, a lower alkyl ester, for example the methyl or ethyl ester. When the acid itself is used as starting material the reaction is preferably carried out in the presence of a condensing agent, for example a carbodiimide, or a 2-alkoxy-1-alkoxycarbonyl-1,2-dihydroquinoline, or 1,1'-carbonyldiimidazole.

The second starting material for the above mentioned process of the invention may be obtained by the reaction of the appropriate pyrazine-2-carboxylic acid with an amino-acid ester of the formula:

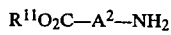

R$^{11}$O$_2$C—A$^2$—NH$_2$ wherein $A^2$ has the meaning stated above and $R^{11}$ is lower alkyl, for example methyl or ethyl, followed by hydrolysis of the ester to the corresponding acid.

An alternative process for the manufacture of an alkanolamine derivative of the invention comprises the reaction of an epoxide of the formula:

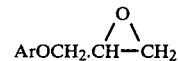

wherein Ar has the meaning stated above, with an amine of the formula:

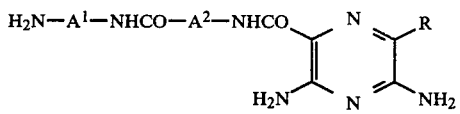

wherein $A^1$, $A^2$ and R have the meanings stated above.

The starting material for the abovementioned reaction may be obtained by the reaction of the starting material for the first process of the invention with a diamine of the formula

H$_2$N—A$^1$—NH$_2$ wherein $A^1$ has the meaning stated above.

Optically-active enantiomorphs of the alkanolamine derivative of the invention may be obtained by the resolution by conventional means of the corresponding racemic alkanolamine derivative of the invention.

The alkanolamine derivative in free base form may be converted into an acid-addition salt thereof by reaction with an acid by conventional means.

As stated above, some of the alkanolamine derivatives of the invention, or acid-addition salts thereof, possess $\beta$-adrenergic blocking activity. This may be determined by the effect of a compound in reversing isoprenaline-induced tachycardia in rats or cats, a standard test for the determination of $\beta$-adrenergic blocking activity. Furthermore, as stated above, some of the alkanolamine derivatives of the invention possess diuretic activity, as determined by their effect in increasing urine volume in rats, a standard test for the determination of diuretic activity. At doses of an alkanolamine derivative of the invention which produce effective $\beta$-adrenergic blockade in rats or cats, or diuresis in rats, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chloropromazine and the benzodiazepine sedative drugs, for example chlordiazepoxide and diazepam; vasodilators, for example glyceryl trinitrate, pentaerythritol tetranitrate, isosorbide dinitrate and hydrazine; other diuretics, for example chlorthalidone, bendrofluazide, hydrochlorothiazide and chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; and α-adrenergic blocking agents, for example phentolamine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

Preferred oral dosage forms are tablets or capsules containing between 10 and 100 mg., and preferably 10 mg. or 50 mg., of active ingredient. Preferred intravenous dosage forms are sterile aqueous solutions of the alkanolamine derivative or of a nontoxic acid-addition salt thereof, containing between 0.05% and 1% w/v of active ingredient, and more particularly containing 0.1% w/v of active ingredient.

The invention is illustrated but not limited by the following Examples:

EXAMPLE 1

N,N¹-dicyclohexylcarbodiimide (1.2 g.) was added to a stirred solution of 2-(3,5-diamino-6-chloropyrazine-2-carboxamido)-2-methylpropionic acid (1.36 g.) and N-hydroxysuccinimide (0.9 g.) in dimethylformamide (50 ml.) and the mixture was stirred at laboratory temperature for 1 hour. 1-β-Aminoethylamino-3-α-naphthyloxypropan-2-ol (1.65 g.) was added and the mixture was stirred for a further 18 hours and then filtered. The filtrate was evaporated to dryness under reduced pressure and the residue was partitioned between n-butanol (100 ml.) and 6% w/v aqueous sodium bicarbonate solution (50 ml.). The butanol phase was separated, washed with water (50 ml.) and evaporated to dryness under reduced pressure. The residue was chromatographed on a silica column (Merck '60', 30 g., column 110 mm. long and 30 mm. diameter) using 200 ml. of a 9:1 v/v mixture of chloroform and methanol and then 200 ml. of a 4:1 v/v mixture of chloroform and methanol as eluants. The fractions containing a product with an $R_f$ of 0.2 when examined by thin layer chromatography using the latter solvent system were collected, combined and evaporated to dryness under reduced pressure. The residue was crystallised from ethanol (50 ml.) and there was thus obtained 3,5-diamino-6-chloro-N-{1-[N-β-(2-hydroxy-3-α-naphthyloxypropylamino)-ethylcarbamoyl]-1-methylethyl}pyrazine-2-carboxamide, m.p. 145°–147° C. (with decomposition).

The 2-(3,5-diamino-6-chloropyrazine-2-carboxamido)-2-methylpropionic acid used as starting material was obtained as follows:

A solutin of 3,5-diamino-6-chloropyrazine-2-carboxylic acid (3.8 g.), N-hydroxysuccinimide (2.4 g.) and N,N¹-dicyclohexylcarbodiimide (4.4 g.) in dimethylformamide (200 ml.) was stirred at laboratory temperature for 1 hour, methyl 1-amino-1-methylpropionate (3.4 g.) and triethylamine (3.0 ml.) were added and the mixture was stirred for a further 18 hours and then filtered. The filtrate was evaporated to dryness and the residue was stirred at laboratory temperature for 18 hours with a solution of sodium hydroxide (1.6 g.) in water (100 ml.) and was then filtered. The filtrate was acidified to pH 3 with aqueous 2 N-hydrochloric acid, and the mixture was filtered. There was thus obtained as solid residue 2-(3,5-diamino-6-chloro-pyrazine-2-carboxamido)-2-methylpropionic acid, m.p. 290°–292° C. (with decomposition).

EXAMPLE 2

The process described in Example 1 was repeated using the appropriate 1-β-aminoethylamino-3-aryloxypropan-2-ol as starting material. There were thus obtained the compounds described in the following table:

Ar—OCH$_2$.CHOH.CH$_2$NH(CH$_2$)$_2$NH—CO—C(CH$_3$)$_2$—NHCO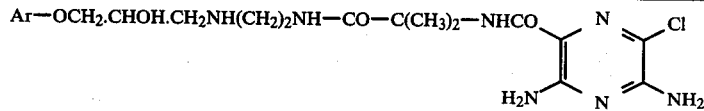

| Ar | m.p. (°C.) | Crystallisation Solvent |
|---|---|---|
| 2-fluorophenyl | 182–184 | ethanol |
| 2-chlorophenyl | 186–187 | methanol |
| 2-methoxyphenyl | 182–185 | acetonitrile |
| 2-tolyl | 185–187 | ethanol |
| 2-ethylphenyl | 172–175 | isopropanol |
| 2-allylphenyl | 133–136 | ethyl acetate |
| phenyl | 192–194 | ethanol |
| 4-acetamidophenyl | 207–208 | methanol |
| 2-naphthyl | 238–239 | methanol |
| 2-t-butylphenyl | 174–176 | methanol |
| 2-allyloxyphenyl | 128–130 | isopropanol |
| 4-chloro-1-naphthyl | 215–217 | methanol |
| 4-methyl-1-naphthyl | 206–208 | methanol |

EXAMPLE 3

A mixture of 1-β-aminoethylamino-3-α-naphthoxypropan-2-ol (0.9 g.) and ethyl β-(3,5-diamino-6-chloropyrazine-2-carboxamido)propionate (0.5 g.) was heated at 90° C. for 25 hours, cooled and chromatographed on a silica column (Merck '60', 20 g., column 50 mm. long and 32 mm. diameter) using the same amounts of the same eluants as described in Example 1. The fractions containing a product with an $R_f$ of 0.2 were collected, combined and evaporated to dryness, and the residue was dissolved in ethanol (20 ml.). The solution was added to a solution of oxalic acid (0.2 g.) in ethanol (20 ml.) and the mixture was filtered. There was thus obtained as solid residue 3,5-diamino-6-chloro-{N-β-[N-(2-hydroxy-3-α-naphthoxy-propylamino)ethyl-carbamoyl]-ethyl}pyrazine-2-carboxamide hydrogen oxalate, m.p. 190°–192° C.

The ethyl β-(3,5-diamino-6-chloropyrazine-2-carboxamido)propionate used as starting material was obtained by a similar process to that described in the second part of Example 1, except that ethyl β-aminopropionate was used in place of methyl 1-amino-1-methylpropionate and that the hydrolysis step using aqueous sodium hydroxide was omitted. The crude reaction product was partitioned between a 2:1 v/v mixture of n-butanole and 6% w/v aqueous sodium bicarbonate solution and the butanol phase was washed with water and evaporated to dryness under reduced pressure. The residue was crystallized from a 3:1 v/v mixture of ethanol and water and there was thus obtained ethyl β-(3,5-diamino-6-chloro-pyrazine-2-carboxamido)propionate, m.p. 155°–157° C.

EXAMPLE 4

The process described in Example 3 was repeated using the appropriate 1-β-aminoethylamino 3-aryloxypropan-2-ol and the appropriate (3,5-diamino-6-chloropyrazine-2-carboxamido)alkanoate ester as starting materials, and omitting the salt formation step. There were thus obtained the compounds described in the following table:

Ar—OCH₂.CHOH.CH₂NH(CH₂)₂NH—CO—A²—NHCO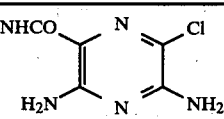

| Ar | A² | m.p. (°C.) | Crystallisation Solvent |
|---|---|---|---|
| 2-chlorophenyl | —CH₂CH₂— | 169–172(d) | ethanol |
| 2-chlorophenyl | —CH₂— | 160–163 | ethanol |
| 1-naphthyl | —CH₂— | 180–182 | ethanol |

In the case of the last two compounds in the above table (wherein —A²— is —CH₂—), the chromatographic purification of the product was omitted. The crude reaction product was stirred with a mixture of chloroform (45 ml.) and methanol (5 ml.) and the solid product filtered off.

Methyl (3,5-diamino-6-chloropyrazine-2-carboxamido)acetate used as starting material for the preparation of the last two compounds in the above table was obtained by a similar procedure to that described above for the preparation of the corresponding ethyl propionate, except that methyl glycinate hydrochloride was used as starting material in place of ethyl β-aminopropionate. Methyl (3,5-diamino-6-chloropyrazine-2-carboxamido)acetate has m.p. 189°–191° C. after crystallisation from a 2:1 v/v mixture of water and methanol.

EXAMPLE 5

A stirred mixture of 2-(3,5-diamino-6-chloropyrazine-2-carboxamido)-2-methylpropionic acid (1.4 g.), 2-ethoxy-1-ethoxycarbonyl-1,2-dihydroquinoline (1.24 g.), 1-β-aminoethylamino-3-o-isopropylphenoxypropan-2-ol (1.4 g.) and dimethylsulphoxide (30 ml.) was heated at 70° C. for 4 hours and then poured into water (500 ml.). The mixture was extracted three times with n-butanol (100 ml. each time) and the combined extracts were washed with water (200 ml.) and evaporated to dryness under reduced pressure. The residue was stirred with methylene chloride (100 ml.), the mixture was filtered and the solid residue was crystallised from isopropanol. There was thus obtained 3,5-diamino-6-chloro-N-{1-[N-β-(2-hydroxy-3-o-isopropylphenoxypropylamino)-ethylcarbamoyl]-1-methylethyl}pyrazine-2-carboxamide, m.p. 152°–153° C.

The process described above was repeated using the appropriate 1-β-aminoethylamino-3-aryloxypropan-2-ol as starting material, and there were thus obtained the compounds of the formula stated in Example 2 described in the following table:

| Ar | m.p. (°C.) | Crystallisation Solvent |
|---|---|---|
| 2,3-dichlorophenyl | 222–226 | ethanol/water/acetonitrile |
| 3,4-dichlorophenyl | 227–229 | ethanol |
| 5-indanyl | 228.5–230 | methanol |
| 1,2,3,4-tetrahydronaphth-5-yl | 149–152 | acetonitrile |
| 1,2,3,4-tetrahydronaphth-6-yl | 222–224 | methanol |
| 4-benzo[b]thienyl | 174–176 | acetonitrile |

The process described above was repeated using the appropriate 1-β-aminoethylamino-3-aryloxypropan-2-ol as starting material, but using 2-isobutoxy-1-isobutoxycarbonyl-1,2-dihydroquinoline instead of 2-ethoxy-1-ethoxycarbonyl-1,2-dihydroquinoline and heating the mixture for 20 hours. There were thus obtained the compounds of the formula stated in Example 2 described in the following table:

| Ar | m.p. (°C.) | Crystallisation Solvent |
|---|---|---|
| 2-carbamoylphenyl | 201–203 | methanol |
| 2-cyanophenyl | 191–193 | ethanol/diethyl ether |

EXAMPLE 6

A mixture of 2-(3,5-diamino-6-chloropyrazine-2-carboxamido)-2-methylpropionic acid (1.35 g.), 1,1'-carbonyldiimidazole (0.9 g.) and dimethyl-formamide (30 ml.) was stirred at laboratory temperature for 90 minutes, a solution of 1-β-aminoethylamino-3-o-acetylphenoxypropan-2-ol (1.65 g.) in dimethylformamide (10 ml.) was added and the mixture was stirred at laboratory temperature for 16 hours and then evaporated to dryness under reduced pressure. The residue was dissolved in ethanol (10 ml.), crushed ice (20 g.) was added and the solvent was decanted off to leave an oily residue which was evaporated to dryness under reduced pressure. The residue was stirred with methanol (30 ml.), the mixture was filtered and the solid residue was crystallised from methanol. There was thus obtained 3,5-diamino-6-chloro-N-{1-[N-β-(3-o-acetylphenoxy-2- hydroxypropylamino)ethylcarbamoyl]-1-methylethyl}-pyrazine-2-carboxamide, m.p. 190°–192° C.

The process described above was repeated using the appropriate 1-β-aminoethylamino-3-aryloxypropan-2-ol as starting material, and there were thus obtained the compounds of the formula stated in Example 2 described in the following table:

| Ar | m.p. (°C.) | Crystallisation Solvent |
| --- | --- | --- |
| 4-carbamoylmethylphenyl | 175–176.5 | methanol |
| 2-acetamidophenyl | 147.5–149.5 | ethanol |
| 2,4-dichloronaphth-1-yl | 194–196 | isopropanol |
| 1,2,3,4-tetrahydro-2,3-dihydroxy-naphth-5-yl | 134–135 | isopropanol |
| indan-4-yl | 199–201 | methanol |
| 1,4-benzodioxan-5-yl | 213–215 | methanol |
| indol-4-yl | 122–124 | isopropanol |
| 4-morpholino-1,2,5-thiadiazol-3-yl | 167–169 | methanol |

EXAMPLE 7

N,N′-Dicyclohexylcarbodiimide (1.15 g.) and then 1-hydroxybenzotriazole hydrate (1.15 g.) were successively added to a stirred solution of 2-(3,5-diamino-6-chloropyrazine-2-carboxamido)-2-methylpropionic acid (1.35 g.) and 1-β-aminoethylamino-3-(7-methylindan-4-yloxy)propan-2-ol (2.0 g.) in dimethylformamide (50 ml.) and the mixture was stirred at laboratory temperature for 20 hours and then filtered. The filtrate was evaporated to dryness under reduced pressure and the residue was partitioned between n-butanol (100 ml.) and aqueous 6% w/v sodium bicarbonate solution (50 ml.). The organic phase was separated, washed with water (50 ml.) and evaporated to dryness under reduced pressure. The residue was crystallised from methanol and there was thus obtained 3,5-diamino-6-chloro-N-{1-[N-β-(2-hydroxy-3-[7-methylindan-4-yloxy]-propylamino)ethylcarbamoyl]-1-methylethyl}pyrazine-2-carboxamide, m.p. 206°–208° C.

EXAMPLE 8

A mixture of (S)-2-(3,5-diamino-6-chloropyrazine-2-carboxamido)propionic acid (1.3 g.), 1-β-aminoethylamino-3-(2,3-dichlorophenoxy)propan-2-ol and tetrahydrofuran (25 ml.) was heated under reflux until all solid had dissolved, 2-ethoxy-1-ethoxycarbonyl-1,2-dihydroquinoline (1.6 g.) was added and the mixture was heated under reflux for 16 hours and then evaporated to dryness under reduced pressure. The residue was partitioned between n-butanol (100 ml.) and aqueous 6% w/v sodium bicarbonate solution (50 ml.) and the organic layer was separated, washed twice with water (50 ml. each time) and evaporated to dryness under reduced pressure. The residue was heated under reflux with diethyl ether (100 ml.) for 30 minutes, the ether was removed by decantation and the residue was crystallised from acetonitrile. There was thus obtained 3,5-diamino-6-chloro-N-{(S)-1-[N-β-(2-hydroxy-3-[2,3-dichlorophenoxy]propylamino)ethylcarbamoyl]ethyl}-pyrazine-2-carboxamide, m.p. 111°–115° C.

The (S)-2-(3,5-diamino-6-chloropyrazine-2-carboxamido)propionic acid (m.p. 240°–242° C. with decomposition) used as starting material was obtained by a similar process to that described in the second part of Example 1, except that L-alanine methyl ester was used in place of methyl 1-amino-1-methylpropionate.

The process described above was repeated using either 1-β-aminoethylamino-3-α-naphthyloxypropan-2-ol or 1-β-aminoethylamino-3-β-naphthyloxy-propan-2-ol as starting material in place of the 2,3-dichlorophenoxy compound. There were thus obtained 3,5-diamino-6-chloro-N-{(S)-1-[N-β-(2-hydroxy-3-α-naphthyloxypropylamino)ethylcarbamoyl]ethyl}pyrazine-2-carboxamide, m.p. 88°–92° C. after crystallisation from methylene chloride, and 3,5-diamino-6-chloro-N-{(S)-1-[N-β-(2-hydroxy-3-β-naphthyloxypropylamino)ethylcarbamoyl]ethyl}pyrazine-2-carboxamide, m.p. 150°–152° C. after crystallisation from ethanol.

The process described above was repeated using 1-β-aminoethylamino-3-α-naphthyloxypropan-2-ol and (R)-2-(3,5-diamino-6-chloropyrazine-2-carboxamido)-propionic acid (m.p. 240.5°–242° C., prepared as described above from D-alanine methyl ester) as starting materials. There was thus obtained 3,5-diamino-6-chloro-N-{(R)-1-[N-β-(2-hydroxy-3-α-naphthyloxypropylamino)ethylcarbamoyl]ethyl}pyrazine-2-carboxamide, m.p. 83°–86° C. after crystallisation from methylene chloride.

EXAMPLE 9

A stirred mixture of (S)-2-(3,5-diamino-6-chloropyrazine-2-carboxamido)-3-phenylpropionic acid (1.8 g.), 1-β-aminoethylamino-3-α-naphthyloxypropan-2-ol (1.43 g.), 2-isobutoxy-1-isobutoxycarbonyl-1,2-dihydroquinoline (1.5 g.) and dimethylsulphoxide (30 ml.) was heated at 75° C. for 18 hours, cooled and poured into ice-water (600 ml.). Aqueous 6% w/v sodium bicarbonate solution (50 ml.) was added, the mixture was filtered and the solid product was washed with diethylether (100 ml.). There was thus obtained as solid product 3,5-diamino-6-chloro-N-{1-[N-β-(2-hydroxy-3-α-naphthyloxypropylamino)ethylcarbamoyl]-2-phenylethyl}pyrazine-2-carboxamide, m.p. 142°–146° C.

The (S)-2-(3,5-diamino-6-chloropyrazine-2-carboxamido)-3-phenylpropionic acid used as starting material was obtained as follows:

Triethylamine (3.0 g.) was added to a stirred solution of 3,5-diamino-6-chloropyrazine-2-carboxylic acid (5.66 g.), L-phenylalanine ethyl ester hydrochloride (6.88 g.) and 2-ethoxy-1-ethoxycarbonyl-1,2-dihydroquinoline (7.4 g.) in dimethylformamide (50 ml.) and the mixture was heated at 75° C. for 3 hours and then at 45° C. for 18 hours, cooled and poured into ice-water (600 ml.). Aqueous 6% w/v sodium bicarbonate solution (100 ml.) was added, the mixture was filtered and the solid residue was crystallised from aqueous methanol. A mixture of the ethyl (S)-2-(3,5-diamino-6-chloro-pyrazine-2-carboxamido)-3-phenylpropionate (m.p. 119°–120° C., 6.0 g.) thus obtained and aqueous 0.2 N-sodium hydroxide solution (150 ml.) was stirred at laboratory temperature for 84 hours and then acidified with acetic acid and filtered. The solid product was crystallised from aqueous ethanol and there was thus obtained (S)-2-(3,5-diamino-6-chloropyrazine-2-carboxamido)-3-phenyl-propionic acid, m.p. 224°–226° C.

EXAMPLE 10

The process described in Example 9 was repeated using (S)-2-(3,5-diamino-6-chloropyrazine-2-carboxamido)-3-hydroxypropionic acid as starting material in place of the corresponding 3-phenylpropionic acid. There was thus obtained 3,5-diamino-6-chloro-N-{1-[N-β-(2-hydroxy-3-α-naphthyloxypropylamino)ethylcarbamoyl]-2-hydroxyethyl}pyrazine-2-carboxamide, m.p. 97°-108° C. after crystallisation from methylene chloride.

The 3-hydroxypropionic acid used as starting material was obtained as follows:

A mixture of 3,5-diamino-6-chloropyrazine-2-carboxylic N,N-diphenylcarbamic anhydride (3.5 g.), L-serine methyl ester hydrochloride (14 g.), triethylamine (0.9 g.) and tetrahydrofuran (50 ml.) was stirred at laboratory temperature for 3 hours, stirred and heated under reflux for 2 hours and then stirred at laboratory temperature for 18 hours and filtered. The filtrate was evaporated to dryness under reduced pressure and the solid residue was washed with aqueous 6% w/v sodium bicarbonate solution and then with diethyl ether. A mixture of the methyl (S)-2-(3,5-diamino-6-chloropyrazine-2-carboxamido)-3-hydroxypropionate (m.p. 191°-194° C., 1.3 g.) thus obtained and aqueous 0.18N-sodium hydroxide solution (75 ml.) was stirred at laboratory temperature for 18 hours and then filtered. The filtrate was acidified to pH 4 with acetic acid, and then to pH 1.5 with aqueous 2N-hydrochloric acid and then filtered. There was thus obtained as solid product (S)-2-(3,5-diamino-6-chloropyrazine-2-carboxamido)-3-hydroxypropionic acid.

EXAMPLE 11

The process described in Example 9 was repeated using (S)-2-(3,5-diamino-6-chloropyrazine-2-carboxamido)-3-methylbutyric acid as starting material in place of the corresponding 3-phenylpropionic acid. There was thus obtained 3,5-diamino-6-chloro-N-{1-[N-β-(2-hydroxy-3-α-naphthyloxypropylamino)ethylcarbamoyl]-2-methylpropyl}pyrazine-2-carboxamide, m.p. 109°-110° C. after crystallisation from a mixture of toluene and diethyl ether.

The 3-methylbutyric acid used as starting material was obtained as follows:

A solution of 3,5-diamino-6-chloropyrazine 2-carboxylic acid (18.9 g.), N-hydroxysuccinimide (17.25 g.) and N,N'-dicyclohexylcarbodiimide (22.7 g.) in dimethylformamide (1 liter) was stirred at laboratory temperature for 4.5 hours, a solution of L-valine (23.4 g.) and 1,1,3,3-tetramethylguanidine (25 ml.) in water (150 ml.) was added and the mixture was stirred for 18 hours and then filtered. The filtrate was evaporated to dryness under reduced pressure, the residue was stirred with water (1 liter) and the mixture was filtered. The filtrate was acidified to pH 4 with acetic acid and the mixture was filtered. The filtrate was further acidified to pH 2 with concentrated aqueous hydrochloric acid and the mixture was filtered. The solid product was crystallised from a 2:1 v/v mixture of water and ethanol and there was thus obtained (S)-2-(3,5-diamino-6-chloropyrazine-2-carboxyamido)-3-methylbutyric acid, m.p. 108°-113° C.

EXAMPLE 12

A mixture of 1-(3,5-diamino-6-chloropyrazine-2-carboxamido)cyclopentanecarboxylic acid (1.5 g.), 1,1'-carbonyldiimidazole (0.9 g.) and dimethyl formamide (25 ml.) was stirred at laboratory temperature for 1 hour, 1-β-aminoethylamino-3-α-naphthyloxypropan-2-ol (1.4 g.) was added and the mixture was stirred at laboratory temperature for 18 hours. Ice-cold aqueous 1% w/v potassium carbonate solution (50 ml.) was added and the mixture was stirred for 1 hour and filtered. The solid residue was crystallised from ethanol and there was thus obtained 3,5-diamino-6-chloro-N-{1-[N-β-(2-hydroxy-3-α-naphthyloxypropylamino)ethylcarbamoyl]cyclopentyl}pyrazine-2-carboxamide, m.p. 203°-204° C.

The cyclopentanecarboxylic acid (m.p. 278°-280° C. after crystallisation from methanol) used as starting material was obtained by a similar process to that described in the second part of Example 11, except that 1-aminocyclopentanecarboxylic acid was used as starting material in place of L-valine.

EXAMPLE 13

A solution of 1,2-epoxy-3-α-naphthyloxypropane (0.6 g.) and 3,5-diamino-6-chloro-N-[1-N-(2-amino-2-methylpropyl)carbamoyl-1-methylethyl]pyrazine-2-carboxamide (1.0 g.) in isopropanol (50 ml.) was heated under reflux for 18 hours and then evaporated to dryness under reduced pressure. The residue was chromatographed on a silica gel column (Merck '60', 75 g., column 18 cm. × 3 cm.) using initially a 19:1 v/v mixture of methylene chloride and methanol (300 ml.) and later a 9:1 v/v mixture of methylene chloride and methanol (500 ml.) as eluants. The fractions containing a product with $R_f$ 0.3 on thin-layer chromatograms using the latter solvent mixture were combined and evaporated to dryness, and the residue was crystallised from acetonitrile. There was thus obtained 3,5-diamino-6-chloro-N-{1-[N-2-(2-hydroxy-3-α-naphthyloxypropylamino)-2-methylpropylcarbamoyl]-1-methylethyl}pyrazine-2-carboxamide, m.p. 130°-131° C.

The pyrazine-2-carboxamide used as starting material was obtained as follows: N,N'-Dicyclohexylcarbodiimide (5.3 g.) was added to a stirred solution of 2-(3,5-diamino-6-chloropyrazine-2-carboxamido)-2-methylpropionic acid (7.2 g.) and N-hydroxysuccinimide (2.9 g.) in dimethylformamide (250 ml.) and the mixture was stirred at laboratory temperature for 1 hour. 2-Methylpropane-1,2-diamine (2.8 g.) was added and the mixture was stirred at laboratory temperature for 18 hours and then filtered. The filtrate was evaporated to dryness under reduced pressure and the residue was partitioned between n-butanol (500 ml.) and aqueous 6% w/v sodium bicarbonate solution (50 ml.). The organic phase was separated, washed twice with water (50 ml. each time) and evaporated to dryness under reduced pressure. The residue was stirred with water (600 ml.) at 85° C. for 10 minutes, and the mixture was cooled and filtered. The filtrate was evaporated to dryness under reduced pressure and the residue was crystallised from isopropanol and then from acetonitrile. There was thus obtained 3,5-diamino-6-chloro-N-[1-N-(2-amino-2-methylpropyl)carbamoyl-1-methylethyl]pyrazine-2-carboxamide, m.p. 202°-204° C.

EXAMPLE 14

N-Hydroxysuccinimide (2.61 g.) and N,N[1]-dicyclohexylcarbodiimide (4.59 g.) were successively added to a stirred solution of 2-(3,5-diamino-6-chloro-pyrazine-2-carboxamido)-2-methylpropionic acid (6.03 g.) in dioxan (205 ml.) at 36° C., and the mixture was stirred at laboratory temperature for 3 hours and then filtered. The filtrate was added to a stirred solution of 1-β-aminoethylamino-3-α-naphthoxypropan-(R)-2-ol (5.73 g.) in dioxan (63 ml.) and the mixture was stirred at 20° C. for 18 hours and then filtered. The solid residue was partitioned between n-butanol (100 ml.) and saturated aqueous sodium bicarbonate solution (100 ml.) and the aqueous layer was separated and extracted twice with n-butanol (50 ml. each time). The combined butanol solutions were then filtered through phase-separating paper, evaporated almost to dryness and filtered. The solid residue was washed with diethyl ether and dried. Part of this solid (3.0 g.) was dissolved in hot ethanol (120 ml.), the solution was filtered and aqueous N-hydrochloric acid (5.7 ml.) was added to the filtrate. The mixture was kept at 20° C. for 18 hours and then filtered and there was thus obtained 3,5-diamino-6-chloro-N-{1-[N-β-(R)-2-hydroxy-3-α-naphthoxypropylamino)ethylcarbamoyl]-1-methylethyl}-pyrazine-2-carboxamide hydrochloride, m.p. 243°–245° C., $[\alpha]_{436}^{24} = +14.0°$ (2% in dimethylformamide).

The 1-β-aminoethylamino-3-α-naphthoxypropan-(R)-2-ol used as starting material was obtained as follows:

A solution of racemic 1-β-aminoethylamino-3-α-naphthoxypropan-(R,S)-2-ol (5.2 g.) in methanol (40 ml.) was added to a stirred solution of (−)-p-toluenesulphonyl-D-asparagine (5.72 g.) in methanol (20 ml.) at 20° C., and the mixture was stirred until complete solution was obtained, and was then allowed to stand at 20° C. for 2 hours and then filtered. The solid product was crystallised twice from methanol (525 ml., then 370 ml.) and the salt thus obtained (m.p. 175°–176° C.) was dissolved in aqueous N-sodium hydroxide solution. The mixture was extracted with ethyl acetate and the extract was dried and evaporated to dryness. The oily residue was extracted with diethyl ether and the extract was evaporated to dryness. There was thus obtained as oily residue 1-β-aminoethylamino-3-α-naphthoxypropan-(R)-2-ol, $[\alpha]_D^{23} = +21.4°$ (4% in aqueous N-hydrochloric acid).

The process described above was repeated using the corresponding (S)-isomer, 1-β-aminoethylamino-3-α-naphthoxypropan-(S)-2-ol ($[\alpha]_D^{23} = 21.4$, prepared as described above for the (R)-isomer but using (+)-p-toluenesulphonyl-L-asparagine as resolving agent), and there was thus obtained 3,5-diamino-6-chloro-N-{1-[N-β-((S)-2-hydroxy-3-α-naphthoxypropylamino)ethylcarbamoyl]-1-methylethyl}pyrazine-2-carboxamide hydrochloride, m.p. 243°–245° C., $[\alpha]_{436}^{24} = -14.4$ (2% in dimethylformamide).

What we claim is:

1. An alkanolamine compound of the formula:

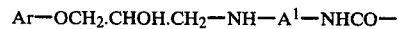

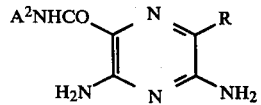

wherein

Ar is phenyl or naphthyl which is unsubstituted or which bears one or two substituents selected from halogen, trifluoromethyl, hydroxy, amino, nitro, carbamoyl, carbamoylmethyl and cyano, and alkyl, alkenyl, alkoxy, alkenyloxy, alkylthio, alkanoyl and alkanoylamino each of up to 6 carbon atoms, or Ar is 4-indolyl, 4-benzo[b]thienyl, 5-benzo[1,4]dioxanyl, 4- or 5-indanyl, 5- or 6-(1,2,3,4-tetrahydronaphthyl), 2,3-dihydroxy-1,2,3,4-tetrahydronaphth-5yl or 4-morpholino-1,2,5-thiadiazol-3-yl;

wherein R is halogen;

wherein $A^1$ is alkylene of 2 to 6 carbon atoms; and wherein $A^2$ is alkylene of 1 to 7 carbon atoms which is unsubstituted or bears a phenyl, hydroxy or carbamoyl substituent, or $A^2$ is cycloalkylene of 3 to 6 carbon atoms;

or an acid-addition salt thereof.

2. An alkanolamine derivative as claimed in claim 1 wherein

Ar is unsubstituted naphthyl, or Ar is phenyl which is unsubstituted or which bears one halogen, carbamoyl, carbamoylmethyl, cyano, alkyl, alkoxy, alkenyl, alkenyloxy, alkanoyl or alkanoylamino substituent, or Ar is 4-indolyl, 4-benzo[b]thienyl, 5-benzo[1,4]dioxanyl, 4-indanyl, 5-(1,2,3,4-tetrahydronaphthyl), 2,3-dihydroxy-1,2,3,4-tetrahydronaphth-5-yl or 4-morpholino-1,2,5-thiadiazol-3-yl;

wherein R is chlorine;

wherein $A^1$ is ethylene or 1,1-dimethylethylene[—C(CH$_3$)$_2$—$CH_2$—];

and wherein $A^2$ is methylene, ethylene, ethylidene[—CH(CH$_3$)—] or 1-methylethylidene [—C(CH$_3$)$_2$—];

or an acid-addition salt thereof.

3. An alkanolamine derivative as claimed in claim 1 wherein Ar and $A^1$ have the meanings stated in claim 1, wherein R is chlorine and wherein $A^2$ is —CR$^1$R$^2$—, wherein R$^1$ is hydrogen or alkyl of up to 3 carbon atoms and R$^2$ is alkyl of up to 3 carbon atoms which is unsubstituted or which bears a phenyl, hydroxy or carbamoyl substituent, or R$^1$ and R$^2$ are joined to form alkylene of 2 to 5 carbon atoms, or an acid-addition salt thereof.

4. The compound 3,5-diamino-6-chloro-N-{1-[N-β-(2-hydroxy-3-α-naphthoxypropylamino)ethylcarbamoyl]-1-methylethyl}pyrazine-2-carboxamide or an acid-addition salt thereof.

5. An acid-addition salt as claimed in claim 1 which is hydrochloride, hydrobromide, phosphate, sulphate, oxalate, lactate, succinate, tartrate, acetate, salicylate, citrate, benzoate, β-naphthoate, adipate or 1,1-methylene-bis-(2-hydroxy-3-naphthoate), or a salt derived from a sulphonated polystyrene resin.

6. A pharmaceutical composition comprising as active ingredient at least one alkanolamine derivative or an acid-addition salt thereof, claimed in claim 1 in association with a pharmaceutically-acceptable diluent or carrier therefor.

7. A method for the treatment of heart disease or hypertension in a warm-blooded animal which comprises administering to said animal an effective amount of at least one compound claimed in claim 1.

* * * * *